United States Patent [19]

Wang et al.

[11] Patent Number: 4,598,369

[45] Date of Patent: Jul. 1, 1986

[54] TOMOGRAPHY APPARATUS AND METHOD

[75] Inventors: Shih-Ping Wang, Los Altos, Calif.; Russell H. Morgan, Baltimore, Md.; Donald F. Specht, Los Altos, Calif.

[73] Assignee: Picker International, Inc., Cleveland, Ohio

[21] Appl. No.: 490,457

[22] Filed: May 2, 1983

[51] Int. Cl.⁴ .................. G06F 15/42; H04N 5/32; G03B 42/02; H05G 1/60

[52] U.S. Cl. ..................... 364/414; 378/22; 378/23

[58] Field of Search ............ 378/22, 23; 364/414

[56] References Cited

U.S. PATENT DOCUMENTS

| | | | |
|---|---|---|---|
| 3,499,146 | 3/1970 | Richards | 378/23 |
| 3,818,220 | 6/1974 | Richards | 378/23 |
| 3,873,834 | 3/1975 | Dammann et al. | 378/23 |
| 4,167,672 | 9/1979 | Richards | 378/23 |
| 4,188,640 | 2/1980 | Dittrich et al. | 378/23 X |
| 4,207,595 | 6/1980 | Dittrich et al. | 378/22 X |
| 4,485,480 | 11/1984 | Kohno et al. | 378/22 X |
| 4,516,261 | 5/1985 | Harding et al. | 364/414 X |

FOREIGN PATENT DOCUMENTS

1523764  9/1978  United Kingdom.

OTHER PUBLICATIONS

Pond, G. D., "Dynamic Linear Tomography and Routine Linear Tomography: A Clinical Comparison", SPIE, vol. 223, Application of Optical Instrumentation in Medicine VIII, 1980, 75–79.

Barrett, H. H. et al., "Radiological Imaging—The Theory of Image Formation, Detection, and Processing", vol. 2, Academic Press, 1981, 368–371.

Capp, M. P. et al., "Photoelectronic Radiology Department", SPIE, vol. 314, Digital Radiography, 1981, 2–8.

Kruger, R. A. et al., "Dynamic Tomographic Digital Subtraction Angiography Using Temporal Filtration", Radiology, vol. 147, No. 3, Jun. 1983, 863–867.

Maravilla, K. R. et al., "Digital Tomosynthesis: Technique for Electronic Reconstructive Tomography", American Journal of Neurological Radiology, 4:883–888, Jul./Aug. 1983.

Chakraborty, D. P. et al., "Self-masking Subtraction Tomosynthesis", Radiology, vol. 140, No. 1, Jan. 1984, 225–229.

Maravilla, K. R. et al., "Digital Tomosynthesis: Technique Modifications and Clinical Applications for Neurovascular Anatomy", Radiology, vol. 152, No. 3, Sep. 1984, 719–724.

Kruger, R. A. et al., "Tomosynthesis Applied to Digital Subtraction Angiography", Radiology, vol. 152, No. 3, Sep. 1984, 805–808.

Primary Examiner—Charles E. Atkinson
Assistant Examiner—Clark A. Jablon
Attorney, Agent, or Firm—Timothy B. Gurin

[57] ABSTRACT

Tomographic images are obtained at a plane of interest by taking a series of x-ray exposures, producing a series of multiple images therefrom, arranging these multiple images so that points residing within a desired plane of interest are coincident to form a first order clarified image, repeating the step for a predetermined number of other planes which are parallel to the first plane of interest, to produce a first order clarified image for each of these planes, and then producing a smeared image for each of such planes, except one, by replicating the first order image for said plane a predetermined number of times and shifting each of the replicated images in the plane as a function of the distance between that particular plane and the x-ray source, the distance between that particular plane and the x-ray image device, the same distances but taken relative to a plane of interest, and the distance moved between exposures by the x-ray source. This smeared image for each particular plane is then multiplied by a coefficient and subtracted from the first order image of the plane of interest to form a second order clarified image of the plane of interest.

25 Claims, 8 Drawing Figures

TOMOGRAPHY APPARATUS AND METHOD

DESCRIPTION

1. Technical Field

This invention relates to tomographic devices and more particularly to a tomographic device employing digital video subtraction.

2. Background Art

Digital radiography has recently become known. More recently developed is the concept of digitizing an image on an x-ray intensifier tube, storing that image, taking a subsequent image after the occurrence of an event and then digitally subtracting the first image from the subsequent image to display only the differences between the two images. This technique is particularly useful in angiography. Furthermore, digital tomography has also been the subject of recent patent applications including one by one of the applicants herein, S. P. Wang.

What has not heretofore been available is an apparatus and method combining all of these technologies which will allow the presentation of a diagnostic quality x-ray image taken at any selected parallel plane through the subject merely by selectively combining a plurality of discrete x-ray images which have been taken, digitized and stored. Heretofore, a series of sets of x-ray exposures were required to be made for each plane of interest through the subject.

Not only is this procedure extremely complicated it also creates total dosage problems to the patient. What is required is a tomographic apparatus which will allow the user to arbitrarily select the plane of interest to be imaged and furthermore to allow the user to easily vary that plane of interest without taking further x-ray exposures.

DISCLOSURE OF INVENTION

The above problems of prior art methods and apparatus for taking tomographic images are overcome by the present invention of a tomographic method and apparatus which uses a radiation source to take a series of co-planar images of a subject from different, predetermined locations, store each of said images, and form a first clarified image by shifting and superimposing the stored images to cause all of the corresponding points in a given first plane of interest through the subject to appear as approximately coincident. These first combined images are then stored, as for example, digital signals in a computer memory.

A second, once clarified image is then formed by shifting and superimposing the stored images to cause all of the corresponding points in a given second plane through the subject, which is parallel to the first plane, to appear to be approximately coincident. This second, once clarified image is also stored in the same manner.

A smeared image is then formed by reproducing the second image from storage a predetermined number of times, corresponding to the number of co-planar images for example, shifting each of the reproduced second images to different positions in the second plane as a function of the distance between the radiation source and the second plane, the distance between the second plane and the co-planar images, the same distances but taken in regard to the first plane and the respective distances traveled by the radiation source in producing each of the original series of co-planar images. This smeared image is then intensity scaled and subtracted from the once clarified first image. The first order clarifying and smearing steps are repeated according to the method of the invention for a predetermined number of parallel planes which are also then intensity scaled and subtracted from the plane of interest. This will produce a second order clarified image of the plane of interest which is essentially free of noticeable artifacts from the images of portions of the subject which are located above and below the plane of interest.

Another embodiment of this invention is to repeat all of the steps recited above for a predetermined number of planes of interest to provide second order clarified images for all of such planes of interest. The process can then be repeated successively for a particular plane of interest by treating these twice clarified images in the same way as the original co-planar images were treated and can be continued until the user can empirically determine that no further clarification is necessary or desirable.

In the preferred embodiment of the invention the apparatus used to carry out this process comprises the combination of a radiation source and a radiation image display apparatus for generating the first series of co-planar images of the subject from predetermined locations and an image digital processing apparatus. This image digital processing apparatus comprises means for converting each of the displayed images into representative sets of digital pixel data, storage means for electronically storing the sets of pixel data and digital processor means for manipulating these sets of pixel data in the manner described above to produce the ultimately clarified images. The digital processor means also controls the radiation apparatus as well as a recording device such as a multiformat camera.

In the preferred embodiment of the invention the radiation source is an x-ray generator tube and the image display apparatus is a proximity type x-ray image intensifier tube. Such tubes are well known such as that described in U.S. Pat. Nos. 4,140,900, 4,255,666 and co-pending application Ser. No. 194,909, now U.S. Pat. No. 4,426,721 entitled X-Ray Intensifier Detector System for X-ray Electronic Radiography.

It is therefore an object of the present invention to provide an improved digital tomographic system.

It is yet another object of the invention to provide a tomographic system capable of producing images at any selected parallel plane through the subject with a single set of x-ray exposures.

It is yet another object of the invention to provide a method and apparatus for digitally obtaining a tomographic image of a patient.

The novel features which are believed to be characteristic of the invention, both as to organization and method of operation, together with further advantages thereof, will be better understood from the following drawings, in which several preferred embodiments of the invention are illustrated by way of example.

BEST MODE FOR CARRYING OUT THE INVENTION

Figure 1:
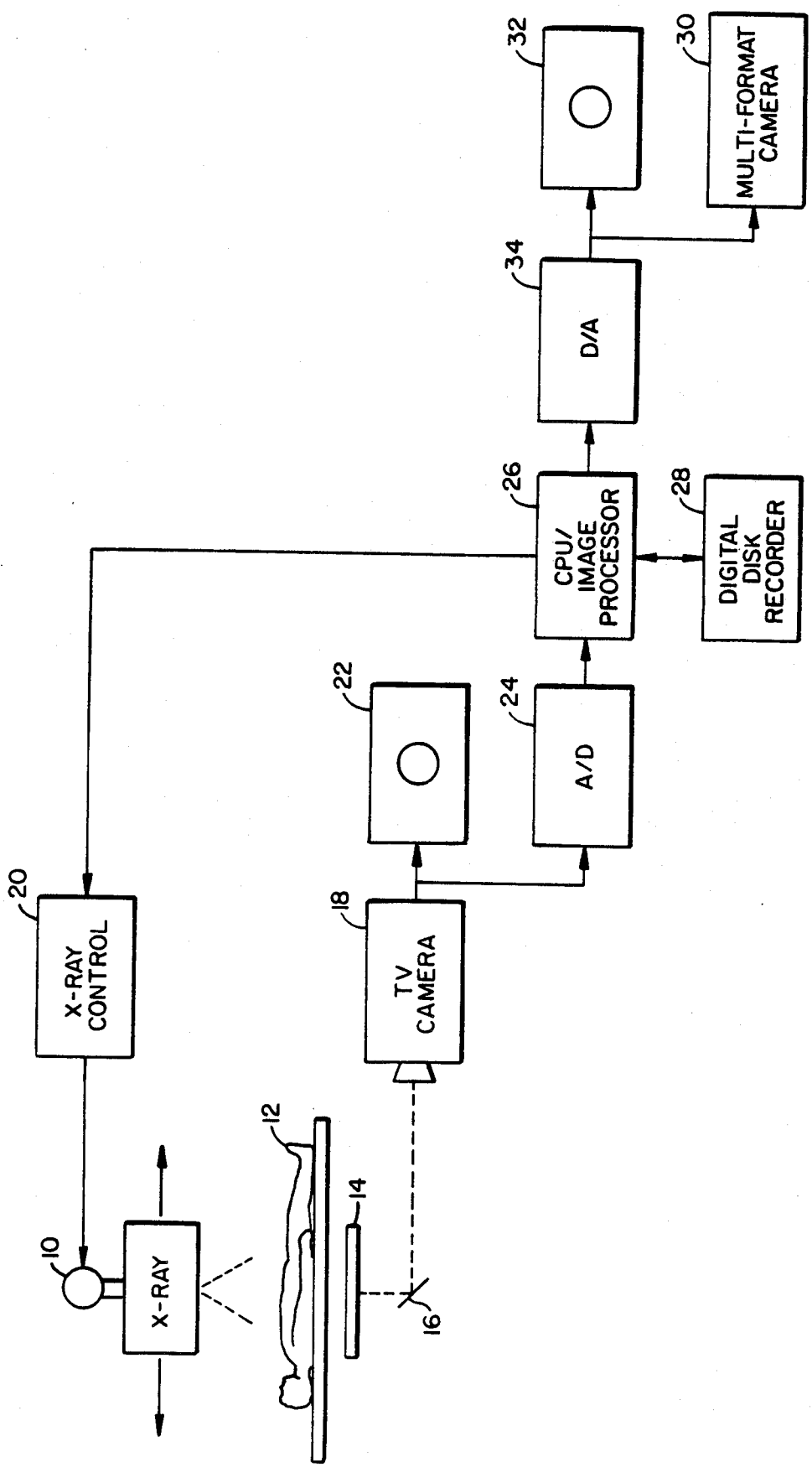
FIG. 1 is a block diagram of the digital tomographic system according to the invention.

Referring now more particularly to FIG. 1, a digital radiography system is depicted in which an x-ray source 10 is caused to make a series of x-ray exposures while moving relative to the patient 12. These exposures are imaged onto a proximity type x-ray image intensifier tube 14 of the type referred to above. In making the series of x-ray exposures the x-ray generator 10 always points to the center of the input screen of the tube 14.

The x-ray images made from each exposure are displayed on the output display screen of the tube 14 and are reflected by mirror 16 to a television camera 18 which has been adjusted to have a low spatial distortion. The output of the camera 18 is supplied to a high definition monitor 22 and to the input of an analog to digital converter 24 whose digital output is supplied to a combined CPU/image, digital processor 26. The duration of the exposure, the timing of the exposure, and the distance traveled between exposures by the x-ray generator 10 is all controlled by a circuit 20 operated by the CPU/image processor 26. A digital disk recorder 28 receives data from and supplies data to the CPU/image, digital processor 26. Data from the CPU/image processor 26 is also supplied through a digital to analog converter 34 to a multi-format camera 30 and to a high definition video monitor 32.

The basic device depicted in FIG. 1, other than the controls for the movement of the x-ray generator 10, is substantially similar to prior art digital subtraction radiography systems such as those manufactured by Xonics Imaging Inc. Model DR10 or Diasonics Model DF100. Where the present invention differs from such prior art systems is in the taking of a series of multiple exposures with the x-ray generator 10 moved to a series of positions, digitizing those exposures, storing them in the computer memory, and then manipulating the series of images derived from those exposures in such a way that a tomographic image can be selectively produced at any desired plane through the subject 12 while images from portions of the patient both above and below the plane of interest are digitally subtracted from the image of interest. How this is done will now be explained in greater detail.

It is known in the art that an infinite number of laminagrams can be made from a finite number of radiographs by taking a series of radiographs of an object from different angles, while the films bear a constant relation to the object. The resulting films are photographed on a composite photograph so that only the plane of interest is in register. Thus an infinite number of such planes can be chosen simply by the arrangement of the photographs during the making of the composite photograph. This prior art process is illustrated diagrammatically in FIG. 2.

Figure 2:
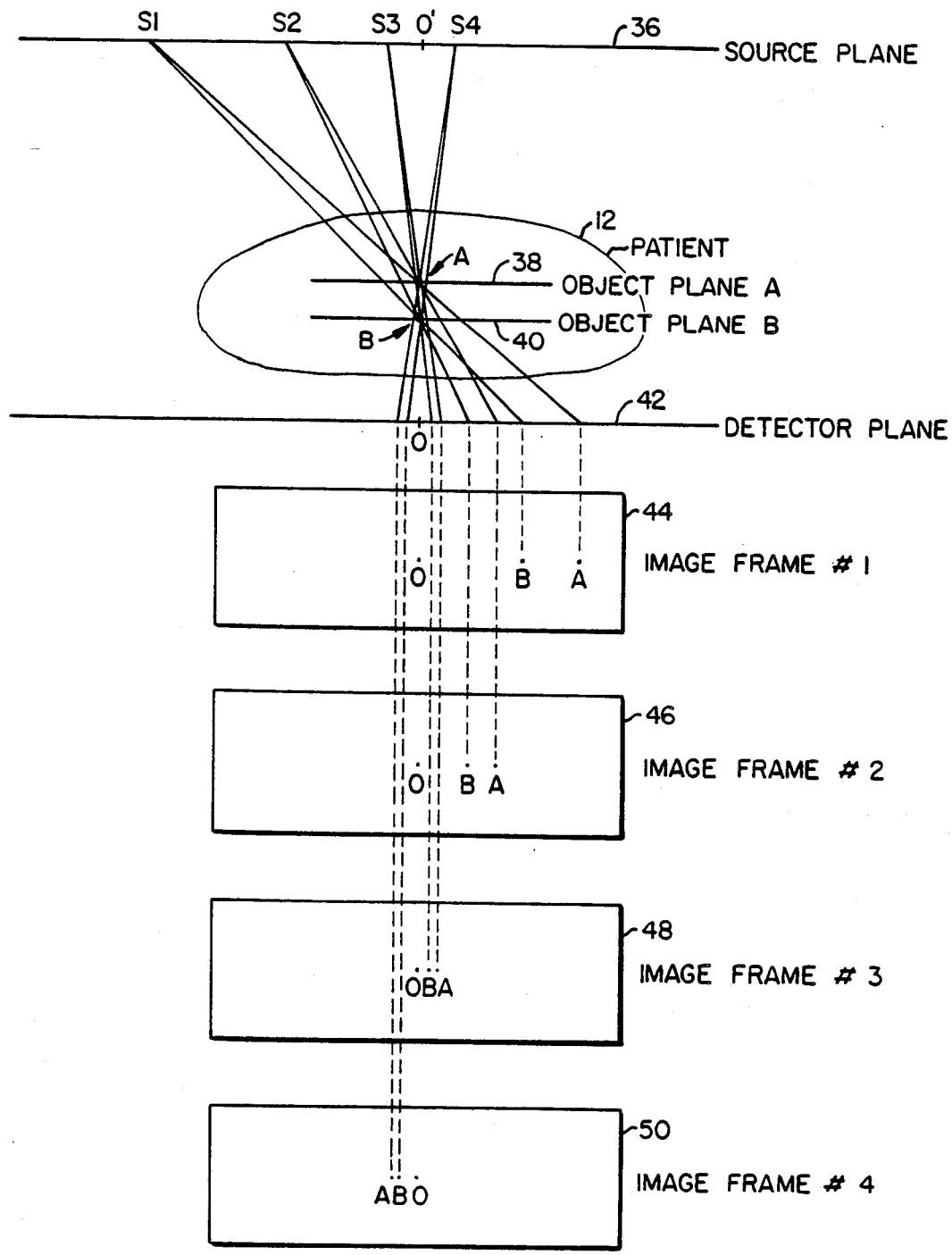
FIG. 2 is a diagramatic illustration showing the production of the series of co-planar x-ray images.

Referring more particularly to FIG. 2, for purposes of the explanation of the method and apparatus according to the invention assume that the x-ray generator 10 takes a series of four exposures denoted $S_1$, $S_2$, $S_3$ and $S_4$ while moving in a source plane 36. The plane 36, as are all the other planes hereinafter referred to, is perpendicular to the plane of the drawing sheet. In actual practice as many as twenty exposures might be made. At all times the central axis of the x-ray generator is preferably kept pointed at some central point O on the surface of the input screen of the x-ray image intensifier tube which is located at the plane 42. For the purposes of this explanation it will be assumed that the x-ray generator travels only in a linear direction in the single plane 36.

Assume for the purposes of this illustration that the patient body 12 has a distinct point of interest A, located in a single plane 38, and point B located in a single plane 40. The planes 36, 38 and 40 are all parallel to the input surface of the x-ray image intensifier tube which is located at plane 42.

It will be seen that exposure number $S_1$ will produce an x-ray image 44 in which the points A, B and O appear at first locations. Similarly, exposures $S_2$, $S_3$ and $S_4$ will produce x-ray images 46, 48 and 50, respectively, that have the same points but shifted differently with respect to each other because of the shift of the x-ray source from positions $S_1$ to $S_2$ to $S_3$ and $S_4$. The images 44, 46, 48 and 50 have been rotated 90% into the plane of the drawing so that they can be viewed as though looking perpendicularly through plane 42.

Figure 3:
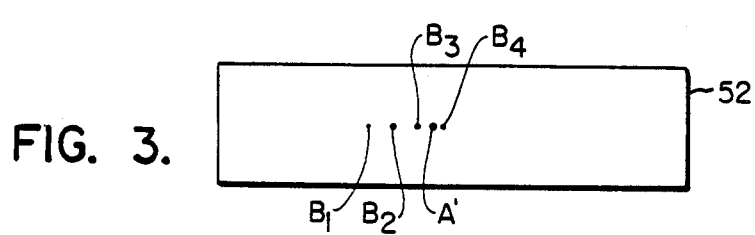
FIGS. 3 through 8, inclusive, are diagramatic illustrations for use in explaining the various operations of the system depicted in FIG. 1.

Referring now to FIG. 3, if the principal plane of interest is plane 38 containing the point A, the x-ray images produced by exposures $S_1$, $S_2$, $S_3$ and $S_4$, for example if they were in the form of radiographs, could be physically superimposed and adjusted so that the points A in each of the x-ray images 44, 46, 48 and 50 were made to be coincident as illustrated in FIG. 3. This produces a first order clarified image of the plane of interest. The points B each appear as separate images in the composite image 52 as denoted by $B_1$, $B_2$, $B_3$ and $B_4$ corresponding to each exposure, respectively.

This same process can be repeated for a plane of interest 40 by rearranging the images depicted in FIG. 3 with appropriate shifting so that all of the points B are coincident. This will, of course, produce a first order clarified image in which all of the points in plane 40 are coincident but all of the points A, produced by the four exposures will not be coincident but will be relatively displaced from each other.

The amount of displacement of each image is a function of the distance between the plane of interest, the x-ray source plane 36 and the detector plane 42. Referring now more particularly to FIG. 4, again assume that point A is one point in the chosen plane, for example plane 38, which we wish to reconstruct. This plane 38 is parallel to the source plane 36 and is a distance $D_A$ from the source plane 36. Plane 38 is also parallel to the detector plane 42 and is a distance $d_A$ away from it.

The procedure for a first order clarification of plane 38 is to shift the different image frames in accordance with the corresponding shift in the source position and then sum the shifted image frames. This is done by first shifting each image frame towards the center (O) of the image frame in the opposite direction as the shift in the source position with respect to the center of the system. Thus as the source $S_N$ moves towards O', the image point $A_N$ at the detector plane 42 will move towards the point O on the detector plane 42. The distance which it will be moved is denoted $(AO)_N$ defined as:

$$(AO)_N = -(SO')_N d_A/D_A$$

where:

$(AO)_N$ is the distance between $A_N$ and center of the detector system, O, and $(SO')_N$ is the distance between the source position at the taking of the $N_{th}$ frame, $S_N$, and the center of the tomography section O'.

This process is repeated for each of the x-ray exposures. Assuming that there were N number of x-ray exposures and thus N image frames to be moved, this process would be repeated N times. All N such shifted image frames for plane 38 are then summed so that each point A in plane 38 will have been enhanced N times while the points outside of plane 38 will be smeared and blurred.

Figure 4:
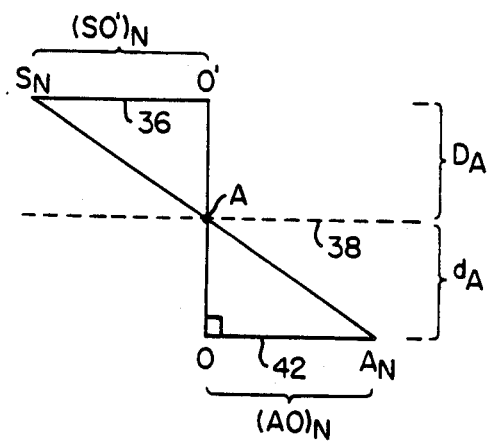
Figure 5:
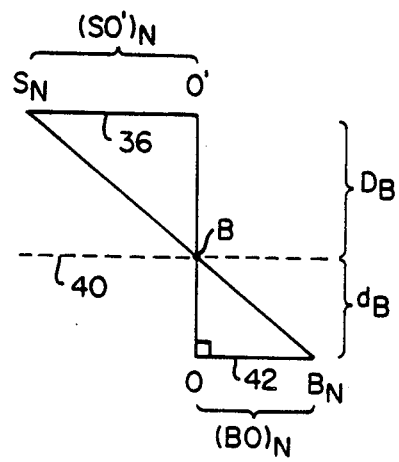

After this first order reconstruction of the plane 38, the same process can be repeated for any other given plane, such as plane 40. As illustrated in FIG. 5, the amount by which the various image frames in plane 40 will have to be shifted is given by a corresponding formula:

$$(BO)_N = -(SO-)_N d_B/D_B$$

Where the terms $(BO)_N$, $D_B$ and $d_B$ have the corresponding meanings as given for FIG. 4.

This process is repeated for plane 40 for each of the N exposures.

The above steps can be repeated for any number of planes through the patient which are parallel to planes 36, 38, 40 and 42.

The operations depicted in FIGS. 2, 3 and 4 can easily be carried out in a digital computer by software programs and methods well known to those skilled in the art. For diagnostic purposes, however, the resultant image still may be unsatisfactory for many diagnostic techniques because of the presence of relatively strong images A or B which are not coincident in the plane of interest. It is at this point that the technique of image subtraction can be utilized.

If the first order clarified image for plane 40 is replicated four times, and the four images are then superimposed on each other but shifted to the positions $B_1$, $B_2$, $B_3$ and $B_4$ shown in FIG. 3 to produce a smeared image, this smeared image can then be subtracted from the image produced in FIG. 3 so that only the coincident points A of plane 38 will remain and the noncoincident points B will be effectively removed. Of course, there will also be a number of noncoincident points A and B derived from each of the four exposures which will also appear as negative artifacts.

Figure 6:
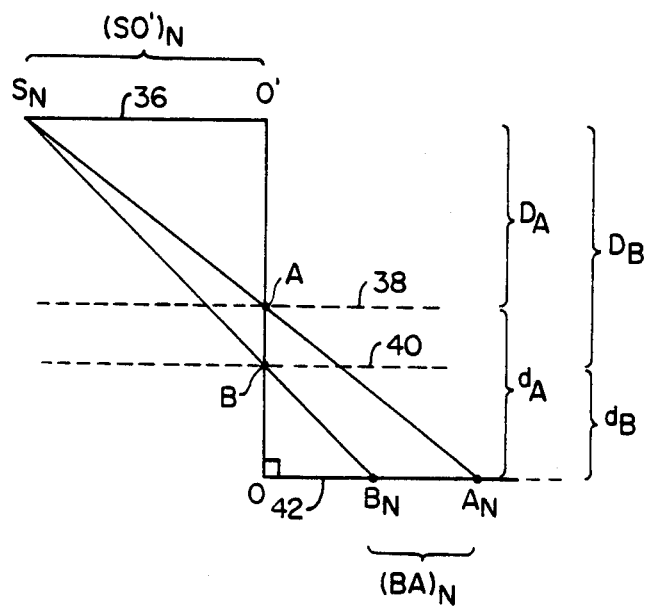

The amount by which each first order clarified image is to be shifted to make up the smeared image is illustrated in FIG. 6. Selecting one of several first order reconstructed images, say for plane 40, then shift the reconstructed image of plane 40 the same number of times as there are exposures (N) according to the formula:

$$(BA)_N = (SO')_N[d_B/D_B - d_A/D_A]$$

All N shifted first order reconstructed images of plane 40 are then summed to form a smeared image. This smeared image is then multiplied by an experimentally determined coefficient, which is less than or equal to 1, and is subtracted from the first order reconstructed plane of interest, plane 38.

The process can thereafter be repeated for several other or all first order reconstructed planes with respect to the plane of interest, plane 38, to ultimately yield a second order reconstructed plane 38.

The amount of the coefficient mentioned above can be experimentally determined by the use of grids and test patterns in place of the patient and then performing the process with different coefficients until an image of the greatest clarity is obtained. This will yield the proper coefficient for use in actual operation with a patient. It is possible to use adaptive techniques to determine the optimum coefficients in an efficient manner.

Figure 7:
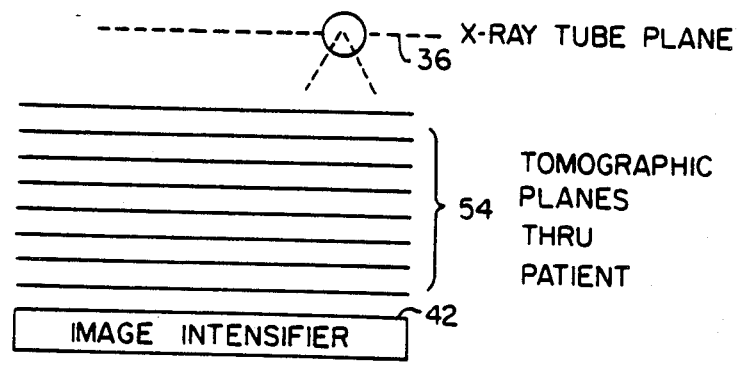

It is also possible to use a correlation method for detection of the tomographic planes. This will be described below. Firstly, the first order planes must be computed as before—namely, the raw data planes are moved until all the features on one level are aligned, and then the displaced raw data planes summed. The result of this step will be a series of first order planes 54 parallel to the image intensifier as illustrated in FIG. 7.

Note that a point which is really on plane i will be reflected on all the other planes in multiple places—a number equal to the number of original exposures.

Although the x-ray tube can be rotated in a two dimensional plane, we will consider first moving it only along a line.

Figure 8:
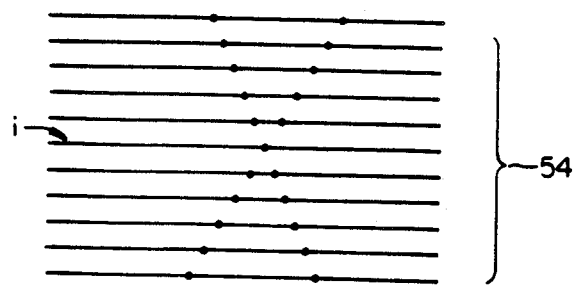

FIG. 8 illustrates a side view of a point on plane i (from only two original exposures in this case). The point is really an "X" in two dimensions. The point can be detected best by correlation of the actual pattern with the known X pattern. If the point is really on level i, the correlation will be high; if it is on some other level, the correlation will be lower. Now plot the value of the correlation cofficient as a point on a secondary correction of plane i. If we then move the theoretical X pattern from left to right to plot all points on the line of plane i, and do the same for all depths into the page, correlation values will have been plotted for every point of the plane i.

If the x-ray tube is moved in a circular pattern above the patient instead of on a straight line, then the X pattern is replaced by a cone through the three-dimensional space of the first order planes. The apex of the cone represents the point on plane i which would generate the cone.

Literally computing the correlation coefficient of the cone with its apex moved to every point in the 3-D space would produce a second generation 3-D space which is much less cluttered than the space defined by the first order planes of FIG. 7.

However, a computationally simpler way to accomplish the same thing is to use the fast Fourier Transform.

It is known that correlation is the same as convolution if the pattern to be correlated is reversed first. Then correlation can be accomplished by multiplying Fourier Transforms.

Therefore: Form the first order tomographic planes. The series of 100 or so "Tomo" planes constitutes the first order 3-D information. Then take the 3-dimensional fast Fourier Transform ("FFT"). Multiply the transform with the pre-stored 3-D transform of the characteristic pattern (such as the cone example above). If the characteristic pattern is symmetrical, it doesn't even have to be flipped prior to transformation. Now take the inverse 3-D transform of the product transform to obtain the corrected 3-D information.

3-D FFT's are, of course, quite straightforward to compute. Just compute 1-D FFT of every row of every plane, then every column, then every line. (Fortunately the three dimensions are separable).

A variation in the second order reconstruction method is to apply a filter function to the original image frames before the shifting is done. Some of these filter functions are quite well known in computerized axial tomography systems, such as the filters proposed by Bracewell and Riddle (1967), Ramachandran-Lakshminarayanan (1971) and Shepp and Logan (1974).

When this process is repeated for even a relatively small number of other planes above and below plane 38 the details of plane 38 will be even more evident whereas the details from other planes will be completely blurred out in a homogeneous background.

The process can be extended by repeating the step for a plurality of planes to produce a whole series of second order clarified images of these planes. Taking these second order images and again subjecting them to the same treatment as the original co-planar images depicted in FIG. 2 will result in a net image for the plane of interest which is an order of magnitude clearer than the second order image for the particular plane of interest.

The techniques by which a visual image, having been digitized and stored on a computer memory, can be processed by software routines are well understood by those skilled in the art and thus will not be described in greater detail. See for example U.S. Pat. No. 4,204,226 and "Computer Electronic Radiography For Early Detection of Vascular Disease," *SPIE Vol.* 173 Application of Optical Instrumentation in Medicine VII (1979), pp. 88–97. It is sufficient to point out that the manipulation of the images to produce a resultant image representative of the superposition of the starting images is done within the computer memory simply by the manner in which the sets of data pixels corresponding to the respective image frames are read out and transposed within the computer's memory. Because the 3-D pixel data can be manipulated in the above recited manner within the computer memory it is also possible to interpolate an oblique plane at any angle through the patient's body.

Although the x-ray generator 10 is only shown in the Figures as having been moved through four exposure locations along a straight line in a single plane 36, it will be appreciated that the x-ray generator 10 can be moved in any pattern, and although preferably it should be moved in a single plane which is parallel to the planes of interest and to the x-ray image intensifier plane, it can also be moved vertically as well as horizontally provided this movement is taken into account in deriving in the appropriate shifting function for the resultant images produced.

The number of planes for which the process is repeated to derive the first order images may be chosen to be larger than the number of first order images used in deriving the second order images. The fewer the number of planes which are operated upon, the less distinct will be the image. On the other hand, if a large number of planes are included within each stage of the processing operation, the memory space of the computer and the processing time will have to be significantly increased.

While a number of currently available devices could be utilized in making up the apparatus of the invention, such as Xonics Imaging, Inc.'s Model DR-10 system, other systems and components could also be used. The processor used could be a Digital Equipment Corporation Model PDP 11/34 or an LSI 11/23. Multiformat cameras of the type depicted as element 30 of the FIG. 1 are made by Illinois Imaging Corporation or Matrix Corporation. Suitable A/D converters for use in digital imaging are also available off the shelf.

Although the foregoing invention has been described in some detail by way of illustration and example for purposes of clarity of understanding, it is understood that certain changes and modifications may be practiced within the spirit of the invention as limited only by the scope of the appended claims.

What is claimed is:

1. A tomographic method comprising the steps of:
   (a) using a radiation source to take a series of co-planar images of a subject from different, predetermined locations,
   (b) forming first order clarified images for each of a plurality of parallel planes through the subject by shifting and superimposing the co-planar images for each such plane to cause all of the corresponding points in each such plane to be approximately coincident,
   (c) for each one of a selected number of planes, forming smeared, first order clarified images by reproducing a predetermined number of times the first order clarified image for the selected plane, and superimposing each of said reproduced first order clarified images shifted in different positions in said selected plane as a function of the distance between the radiation source and said selected plane, the distance between said selected plane and the co-planar images, the same distances but with respect to a particular plane of interest, and the distances traveled by the radiation source in producing the series of co-planar images, and
   (d) multiplying the smeared images by appropriate coefficients and then subtracting them from the first order clarified image of said particular plane of interest to form a second order clarified image of the particular plane of interest.

2. The method as recited in claim 1 comprising the further step e of repeating steps c and d for a predetermined number of particular planes of interest to form a plurality of second order clarified images.

3. The method as recited in claim 2 wherein the steps b, c and d are repeated but with the second order clarified images substituted for the images produced in step a.

4. The method as recited in claims 1 or 2 wherein the steps b, c and d are done automatically within the memory unit of a digital computer.

5. The method as recited in claim 1 wherein step a comprises forming the images on the output display screen of a proximity type image intensifier tube.

6. In combination with a radiation source and radiation image display apparatus for generating a series of co-planar radiation images of a subject from different predetermined locations, image digital processing apparatus comprising:
   (a) means for converting each of said displayed images incident at a detector plane into representative first sets of digital pixel data signals,
   (b) storage means for electronically storing sets of digtal pixel data signals including said first sets of digital data signals,
   (c) digital processor means connected to said storage means for
      (i) recombining said first sets of digital pixel data signals in a manner to produce second sets of digital pixel data signals representative of first order clarified images for each of a series of parallel planes taken through the subject, said first order clarified images for each plane being formed by shifting and superimposing the images to cause all of the points in the plane to be approximately coincident, (ii) replicating the second sets of data signals a plurality of times and recombining them to form third sets of digital data signals for each of said planes which are each representative of a plurality of reproduced first order images each shifted to a different position in the plane as a function of the distance between the plane and the radiation source, the distance between the plane and the co-planar images, the same distances taken with respect to a particular plane of interest, and the distances traveled by the radiation source in producing the series of co-planar images, and (iii) forming a fourth set of digital data signals corresponding to a second order clarified image for said particular plane of interest by subtracting, according to corresponding image elements, the third sets of digital data signals from the second set of digital data signals which corresponds to the particular plane of interest.

7. The combination as recited in claim 6 wherein the image display apparatus comprises a proximity type image intensifier tube.

8. The combination as recited in claim 6 wherein the digital processor performs the same set of operations for a selected plurality of said planes to form a plurality of fourth sets of digital data and then repeats the entire sequence of operations for a selected plane of interest but with said plurality of fourth sets of digital data signals substituted for the first sets of digital data signals.

9. The combination as recited in claim 6 wherein the digital processor, prior to subtracting the third set of digital data signals from the fourth set of digital data signals, reduces the magnitude of said third set of digital data signals by a predetermined scale factor.

10. The combination as recited in claim 6 wherein the digital processor filters said first sets of digital pixel data signals with a Bracewell and Riddle filter.

11. The combination as recited in claim 6 wherein the digital processor filters said first sets of digital pixel data signals with a Ramachandran-Lakshminarayanan filter.

12. The combination as recited in claim 6 wherein the digital processor filters said first sets of digital pixel data signals with a Shepp and Logan filter.

13. The combination as recited in claim 6 wherein the radiation source moves in a plane parallel to the co-planar images and the first order clarified image for any given plane is created by shifting each coplanar image produced during exposure N according to the formula:

$$(AO)_N = -(SO')_N d_A/D_A$$

where:
$N = 1, 2, 3$ up to the total number of exposures;
$(AO)_N =$ the distance between the same image point in each co-planar image and the detector system, O;
$(SO')_N =$ the distance between the source position at the time the co-planar image is produced and the center of tomography section, O';
$D_A =$ the distance from the plane of movement of the radiation source (i.e. the source plane) to the given plane; and
$d_A =$ the distance from the given plane to the detector plane.

14. The combination as recited in claim 13 wherein the third sets of digital data signals correspond to replicated first order clarified images which are each shifted according to the formula:

$$(BA)_N = (SO')_N [d_B/D_B - d_P/D_P]$$

where
$(BA)_N =$ the amount by which each replication of the first order image is shifted for a given exposure position, $S_N$,
where
$D_B =$ the distance between the source plane and the plane corresponding to the first order clarified image,
$d_b =$ the distance between said plane and the detector plane,
$D_P =$ the distance from the source plane to the particular plane of interest, and
$d_p =$ the distance between the plane of the interest and the detector plane.

15. The method as recited in claim 1 wherein during step a the radiation source is moved in a plane parallel to the co-planar images and in step b the first order clarified image for any given plane is created by shifting the co-planar image produced during exposure number N according to the formula:

$$(AO)_N = -(SO')_N d_A/D_A$$

where:
$N = 1, 2, 3$ up to the total number of exposures;
$(AO)_N =$ the distance between the same image point in each co-planar image and the detector system, O;
$(SO')_N =$ the distance between the source position at the time the co-planar image is produced and the center of tomography section, O';
$D_A =$ the distance from the plane of movement of the radiation source (i.e. the source plane) to the given plane; and
$d_A =$ the distance from the given plane to the detector plane.

16. The method as recited in claim 15 wherein the smeared first order clarified images are formed by shifting each of them according to the formula:

$$(BA)_N = (SO')_N [d_B/D_B - d_P/D_P]$$

where
$(BA)_N =$ the amount by which each replication of the first order image is shifted for a given exposure position, $S_N$;
$D_B =$ the distance between the source plane and the plane corresponding to the first order clarified image,
$d_b =$ the distance between said plane and the detector plane,
$D_P =$ the distance from the source plane to the particular plane of interest, and
$d_p =$ the distance between the plane of the interest and the detector plane.

17. The combination as recited in claim 6 wherein the digital processor uses two-dimensional interpolation algorithms to displace images by amounts other than an integral number of pixels in order to minimize registration errors.

18. In combination with a radiation source and radiation image display apparatus for generating a series of co-planar radiation images of a subject from different predetermined locations, image digital processing apparatus comprising:

(a) means for converting each of said displayed images incident at a detector plane into representative first sets of digital pixel data signals, (b) storage means for electronically storing sets of digital pixel data signals including said first sets of digital data signals, (c) digital processor means connected to said storage means for (i) recombining said first sets of digital pixel data signals in a manner to produce second sets of digital pixel data signals representative of first order clarified images for each of a series of parallel planes taken through the subject, said first order clarified images for each plane being formed by shifting and superimposing the images to cause all of the points in the plane to be approximately coincident, (ii) calculating the correlation coefficient for every point on the plane between the theoretical three-dimensional shadow of a single object at the point in question and the actual measured 3-D data as determined up through step i, and (iii) forming a third set of digital data signals corresponding to the correlation coefficient calculated in step ii for every point in the desired plane.

19. The combination as recited in claim 18 wherein the processing is completed in the same way for every point in a plurality of planes, thus generating clarified three-dimensional data.

20. In combination with a radiation source and radiation image display apparatus for generating a series of co-planar radiation images of a subject from different predetermined locations, image digital processing apparatus comprising:

(a) means for converting each of said displayed images incident at a detector plane into representative first sets of digital pixel data signals, (b) storage means for electronically storing sets of digital pixel data signals including said first sets of digital data signals, (c) digital processor means connected to said storage means for (i) recombining said first sets of digital pixel data signals in a manner to produce second sets of digital pixel data signals representative of first order clarified images for each of a series of parallel planes taken through the subject, said first order clarified images for each plane being formed by shifting and superimposing the images to cause all of the points in the plane to be approximately coincident, (ii) computing the three-dimensional discrete Fourier Transform of the first order clarified image, (iii) multiplying this transform by the transform of the spatially-reversed characteristic image of a point in the first order clarified image, (iv) computing the inverse discrete Fourier Transform of the results of step iii, which is the second order clarified 3-dimensional image of interest.

21. The combination as recited in claims 8, 19 or 20 wherein the digital processor is used further to interpolate an oblique plane at any angle through the patient's body using the three-dimensional data stored in the computer's memory.

22. A method of forming a tompgraphic image of a subject under examination comprising the steps of:

(a) taking a plurality of radiographs of an object from different angles to create a series of co-planar images of said object;

(b) forming a first order clarified image of a first plane through the object;

(c) forming a first order clarified image of a second plane through the object;

(d) forming a smeared, first order clarified image of said second plane; and (e) forming a second order clarified image of said first plane by subtracting the smeared, first order clarified image of said second plane from the first order clarified image of said first plane.

23. The method of claim 22 wherein the steps of forming first order clarified images of a plane of interest comprise the step of superimposing and shifting co-planar images of said plane of interest to cause corresponding points in said plane to substantially coincide.

24. The method of claim 22 wherein the step of forming a smeared, first order clarified image comprises the steps of;

(a) replicating the first order clarified image of said second plane a predetermined number of times;

(b) superimposing said first order clarified images; and (c) shifting said superimposed, first order clarified images.

25. The method of claim 22 wherein the smeared, first order clarified image of said second plane is intensity scaled prior to subtraction from the first order clarified image of the first plane.

* * * * *

UNITED STATES PATENT AND TRADEMARK OFFICE
CERTIFICATE OF CORRECTION

PATENT NO. : 4,598,369

DATED : July 1, 1986

INVENTOR(S) : Shih-Ping Wang et al.

It is certified that error appears in the above-identified patent and that said Letters Patent is hereby corrected as shown below:

Column 5, line 17, "$(BO)_N$." should be --$(BO)_N$,--
Column 12, line 16, "tompgraphic" should be --tomographic--

Signed and Sealed this

Sixteenth Day of September 1986

[SEAL]

Attest:

DONALD J. QUIGG

Attesting Officer

Commissioner of Patents and Trademarks